(12) United States Patent
Jerome et al.

(10) Patent No.: US 6,498,262 B2
(45) Date of Patent: Dec. 24, 2002

(54) PROCESS FOR PRODUCING ALUMINUM DIACETATE MONOBASIC

(75) Inventors: James E. Jerome, Ooltewah, TN (US); Glenda L. Fleming, Albany, OR (US); Joel H. Swinson, Evans, GA (US)

(73) Assignee: Chattem Chemicals, Inc., Chattanooga, TN (US)

( * ) Notice: Subject to any disclaimer, the term of this patent is extended or adjusted under 35 U.S.C. 154(b) by 0 days.

(21) Appl. No.: 09/764,156

(22) Filed: Jan. 17, 2001

(65) Prior Publication Data

US 2002/0137960 A1 Sep. 26, 2002

(51) Int. Cl.$^7$ ................................................. C07F 5/06
(52) U.S. Cl. ....................................................... 556/183
(58) Field of Search .......................................... 556/183

(56) References Cited

U.S. PATENT DOCUMENTS

| | | | |
|---|---|---|---|
| 2,844,551 A | * 7/1958 | Orthner et al. | 260/18 |
| 2,918,484 A | 12/1959 | Huehn | 260/448 |
| 2,932,659 A | * 4/1960 | Orthner et al. | 260/414 |
| 2,992,262 A | * 7/1961 | Sears, Jr. et al. | 260/448 |
| 3,014,055 A | 12/1961 | Johnson et al. | 260/448 |
| 3,047,602 A | * 7/1962 | Schenck | 260/448 |
| 3,467,612 A | 9/1969 | Gagliardi | 260/29.6 |
| 3,486,911 A | 12/1969 | Goldstein et al. | 106/2 |
| 3,655,329 A | 4/1972 | Shih et al. | 23/50 B |
| 3,957,598 A | 5/1976 | Merkl | 204/72 |
| 3,959,091 A | * 5/1976 | Merkl | 204/72 |
| 4,224,030 A | 9/1980 | Reinhardt et al. | 8/115.7 |
| 4,327,032 A | * 4/1982 | Lohse et al. | 260/448 R |
| 4,560,783 A | * 12/1985 | Shioyama et al. | 556/183 |
| 4,661,205 A | 4/1987 | Ow et al. | 162/78 |
| 5,069,908 A | 12/1991 | Henley | 421/449 |
| 5,120,544 A | 6/1992 | Henley | 424/443 |
| 5,183,785 A | 2/1993 | Ready | 501/127 |
| 5,233,065 A | 8/1993 | Sharif | 556/183 |

FOREIGN PATENT DOCUMENTS

| | | |
|---|---|---|
| EP | 0 146 964 | 12/1984 |
| EP | 0 148 753 | 1/1985 |
| GB | 452065 | 10/1935 |
| WO | WO 97/41063 | 11/1997 |
| WO | WO 98/47849 | 10/1998 |

OTHER PUBLICATIONS

Maksimov, et al., Zhur. Neorg. Khim., 5:558 (1960) [Russ. J. Inorg. Chem., 267, 1960].
Bumans, et al., Latv. PSR Zinat. Akad. Vestis, Kim. Ser., 2;167–170 (1974); CA 81:32638.
Maksimov, et al., Russ. J. Inorg. Chem. (Engl.), 9(4), 559–60 (1964).
GB Patent Specification No. 1436732 –Preparing Metal–Carboxylic Acid Compoundsm filed May 26, 1976, by George Gergely Merkl.
Aluminum, Its Application in the Chemical and Food Industry, P. Juniere and M. Sigwalt (translated from French by W.C.E. Barnes), Chemical Publishing Company: New York, NY, p. 78, 1964.

* cited by examiner

*Primary Examiner*—Porfirio Nazario-Gonzalez
(74) *Attorney, Agent, or Firm*—Amster, Rothstein & Ebenstein (57) ABSTRACT

The present invention provides a new process for preparing aluminum diacetate monobasic. The process of the invention comprises the steps of: (a) agitating a reaction mixture comprising an aqueous acetic solution and a sodium aluminate solution to form aluminum diacetate monobasic and sodium acetate in the reaction mixture; and (b) adding aluminum chloride solution to the reaction mixture in an amount sufficient to react with sodium acetate to obtain a resulting product comprising aluminum diacetate monobasic.

22 Claims, 3 Drawing Sheets

PROCESS FOR PRODUCING ALUMINUM DIACETATE MONOBASIC

FIELD OF THE INVENTION

The present invention relates to a new process for producing aluminum diacetate monobasic.

BACKGROUND OF THE INVENTION

Many approaches have been described in the literature prior to the present invention for preparing aluminum diacetate monobasic, $Al(C_2H_3O_2)_2(OH)$, which is also known as hydroxyaluminum diacetate, monohydroxy aluminum acetate, or monobasic aluminum acetate. V. N. Maksimov, et al., (1) summarizes most of the methods extant in 1960 as does a more brief description in Junière and Sigwalt's *Aluminium, Its Applications in the Chemical and Food Industry* (2).

In 1854, W. Crum (3) described the first preparative route to aluminum diacetate monobasic by the double displacement reaction of aluminum sulfate with lead acetate. A similar displacement reaction route using barium acetate and aluminum sulfate was described in 1899 by Ley (4).

The most common preparation of $Al(C_2H_3O_2)_2(OH)$ is from aluminum hydroxide (hydrated alumina) and glacial acetic acid (5–8). Sears, U.S. Pat. No. 2,992,262 (9) described a process for making basic aluminum salts, particularly basic aluminum acetates, of short chain carboxylic acids from the reaction of hydrated alumina (i.e., aqueous $Al(OH)_3$) with acetic acid or acetic anhydride, where the acid or anhydride component is introduced in the vapor phase under special conditions.

Another common route for producing aluminum diacetate monobasic is from the reaction of $AlCl_3$ with sodium acetate (10–12). $Al(C_2H_3O_2)_2(OH)$ from aluminum chloride and acetic acid has also been described (13), but is a poor synthesis in terms of yield and purity of the product.

A route that uses the action of acetic anhydride on aluminum nitrate was described by Späth in 1912 (14). A preparative route that reacts aluminum metal with acetic acid was described by Seligman in 1916 (15). Merkil further developed the approach from metallic aluminum as described in U.S. Pat. No. 3,957,598 (16).

In 1974, Bumans and Mironovich (17) described that during hydrothermal syntheses of boehmite from the treatment of bayerite or hydrargillite in 1–7 molar acetic acid for 5 hours at 200° C., basic aluminum acetates were formed when the acetic acid concentration was increased, and that with 100% acetic acid under the same conditions $Al(C_2H_3O_2)_2(OH)$ was formed.

Johnson, U.S. Pat. No. 3,014,055 (18) described a process of forming water soluble complexes of alumina that implies the formation of basic aluminum acetates, although these compositions were made soluble by the incorporation of significant amounts of water soluble, organic, polyhydroxy stabilizing compounds.

Shih, U.S. Pat. No. 3,655,329 (19) described a process for the production of water-soluble, poly aluminum hydroxy (PAH) salts including PAH-acetate. This involved precipitating the PAH compound from a solution of an aluminum halide salt treated with $NH_4OH$, NaOH, or KOH, and then dissolving the PAH compound in one of a selection of acids that includes acetic acid.

U.S. Pat. No. 5,233,065 (20) described a method for producing an aqueous aluminum acetate solution that was stated as being stable to boiling, heating, and aging by the α-hydroxy-carboxylic acid treatment of a composition formed from the reaction of a hydroxychloroaluminum species with glacial acetic acid.

Many of the known processes for preparing aluminum diacetate monobasic are not desirable commercially since they result in a product of low yield or purity, and/or are expensive to produce since they require raw materials that are expensive or are not otherwise available in bulk, or utilize complex, time consuming and/or inefficient processing steps.

SUMMARY OF THE INVENTION

The present invention provides a new process for preparing aluminum diacetate monobasic that, unlike many of the processes of the prior art, results in a product of high yield and purity, utilizes raw materials that are inexpensive and readily available commercially, and includes simple and time efficient processing steps. Specifically, the process of the present invention comprises the steps of: (a) agitating a reaction mixture comprising an aqueous acetic solution and a sodium aluminate solution to form aluminum diacetate monobasic and sodium acetate in the reaction mixture; and (b) adding aluminum chloride solution to the reaction mixture in an amount sufficient to react with sodium acetate to obtain a resulting product comprising aluminum diacetate monobasic.

The aluminum diacetate monobasic obtained by the process of the present invention is water-insoluble and thixotropic, and is useful in a number of applications including but not limited to sol-gels, waste water treatment, papermaking, dyeing, polymer formulations, textile manufacturing, and ink formulations.

Additional objects and benefits of the present invention will be apparent from the description which follows.

DETAILED DESCRIPTION OF THE INVENTION

The process of the invention makes use of two different synthetic routes to prepare aluminum diacetate monobasic. Step (a) of the process employs the reaction of sodium aluminate ($NaAlO_2$) with an aqueous acetic solution (made of acetic acid, acetic anhydride or a combination of acetic acid and acetic anhydride), to form aluminum diacetate monobasic and sodium acetate in the reaction mixture. Step (b) of the process employs the reaction of aluminum chloride ($AlCl_3$) with the sodium acetate existing in solution after step (a). Both reactions are set forth below.

The combined approach of this present invention is unique in that the desired product, $Al(C_2H_3O_2)_2(OH)$, is formed from a strongly basic aluminum precursor (i.e., $NaAlO_2$ in step (a)), followed by the continued formation of the desired product from a strongly acidic aluminum precursor (i.e., $AlCl_3$ in step (b)). $NaAlO_2$ combined with $NaC_2H_3O_2$ (strong base plus weak base) is a very poor route to synthesize aluminum diacetate monobasic as is $AlCl_3$ with acetic acid (two acids) in a non-pressurized system. In addition, the use of $NaAlO_2$ and acetic acid alone to prepare aluminum diacetate monobasic represents a significant waste of acetate. By making use of the driving force of simple acid-base chemistry in both steps (a) and (b), the process of this invention is an effective and relatively simple method of manufacture of $Al(C_2H_3O_2)_2(OH)$. The balanced chemical equation, with steps (a) and (b) combined, for the process of the present invention is as follows:

$$29NaAlO_2+10NaOH+103HC_2H_3O_2+13AlCl_3 \rightarrow \\ 42Al(C_2H_3O_2)_2(OH)+39NaCl+19HC_2H_3O_2+26H_2O$$

This equation is based on using a sodium aluminate solution having a 1.34:1 Na-to-Al ratio. The extra amount of sodium comes from the caustic (NaOH) added to commercial $NaAlO_2$ solutions to prevent precipitation of the concentrated solution. When the sodium aluminate solution is obtained from alternative commercial sources, the Na:Al mole ratio typically varies in the range of 1.1 to 1.5 moles Na per mole Al. This may require adjusting the stoichiometry of the reaction to accommodate the different amount of caustic present. Typically, concentrated sodium aluminate solutions have a Na/Al mole ratio of 1.25–1.35. For purposes of the present invention, the sodium aluminate solution may contain 1–45% by wt. sodium aluminate, and preferably contains 38–45% by wt. sodium aluminate.

Sodium aluminate solutions for use in the process of the present invention are available commercially in a variety of grades and concentrations. These $NaAlO_2$ solutions range from almost colorless to dark brown. The dark or brown coloration is due to organic impurities carried along during the processing of aluminum bearing ore into the sodium aluminate solution. These organic impurities typically include humates and oxalates, as well as other impurities. For convenience, it may be desirable to use a more expensive grade of a sodium aluminate solution that contains minimal impurities. However, if darker, lower quality grades of sodium aluminate solution are used in the process, the present invention provides an additional method for treating the sodium aluminate solution to render it more suitable for use in the process.

Specifically, the present invention provides for subjecting the sodium aluminate solution to treatment with magnesium carbonate ($MgCO_3$) followed by filtration before being admixed with the aqueous acetate solution in step (a). The treatment of sodium aluminate solution with magnesium carbonate first involves heating the sodium aluminate solution (stabilized or unstabilized) to a minimum temperature of 80° C. Magnesium carbonate is then added to the heated sodium aluminate solution at a concentration ranging from 0.005% to 10% by weight, preferably 0.01% to 0.1% by weight, and most preferably about 0.05% by weight. The $MgCO_3$-treated sodium aluminate solution is then agitated for about 30 minutes to 24 hours, and preferably about 30 minutes to 4 hours. The $MgCO_3$-treated sodium aluminate solution may be immediately filtered while hot using a 1 μm filter, for example. Alternatively, the $MgCO_3$-treated sodium aluminate solution may be cooled to a temperature ranging from 80° C. to 25° C., with or without the use of a cooling system. However, the magnesium carbonate treatment is most effective when the treated solution is allowed to cool slowly to ambient temperature over 12–24 hours, and then filtered.

As a result of the magnesium carbonate treatment, the sodium aluminate solution contains significantly less acid-insolubles, base-insolubles, and organic impurities present in the sodium aluminate solution before treatment, and therefore allows for greater purity of the monohydroxy aluminum diacetate product when used in the process of the present invention. In addition, the Na-to-Al ratio of the sodium aluminate solution is minimally affected by this treatment, resulting in a lowering of the Na-to-Al ratio by less than 1%. This change is not significant enough to require altering the calculated reaction stoichiometry for the process determined from the ratio of Na to Al in untreated sodium aluminate solution. The ability provided by this $MgCO_3$-treatment method to maintain a high quality raw material despite multiple sources with various quality levels makes the process of this invention particularly useful as an industrial method of manufacture of aluminum diacetate monobasic.

The aqueous acetic solution used in step (a) may be composed of water mixed with high purity glacial acetic acid, technical grade glacial acetic acid, or more dilute aqueous acetic acid, including side-stream industrial sources of acetic acid, as well as acetic anhydride. The process of this invention requires a slight molar excess (1% to 10%) of acetate ion in order to produce good yield. Enough acetate ion must be present not only to react with the sodium aluminate, forming the desired $Al(C_2H_3O_2)_2(OH)$ material (and to neutralize the excess caustic content present in commercial sodium aluminate solutions), but also to provide sufficient acetate ion to drive the reaction to completion. The 1% to 10% excess acetate ion refers to this additional amount needed to drive the reaction.

The aluminum chloride solution used in step (b) may be prepared by combining water with commercially available aluminum chloride. For purposes of the present invention, the aluminum chloride solution may contain 10–31% by wt. $AlCl_3$, and preferably 25–31% by wt. $AlCl_3$. However, the use of a lower concentration of $AlCl_3$ outside of the preferred range may require longer reaction times and result in lower product yields.

In terms of reaction conditions, step (a) may be conducted at a temperature of 50–105° C., and preferably at a temperature of 95–100° C. Step (b) also may be conducted at a temperature of 50–105° C., although the preferred temperature is again 95–100° C. It is contemplated that the time of reaction for each of step (a) and step (b) is about 1–8 hours. However, about 1 hour for each reaction is preferred. The skilled artisan would appreciate that steps (a) and (b) may be performed at various combinations of time and temperature within the ranges set forth above. It is also contemplated that the process may be accomplished as a continuous process method, or as a batch by batch process. It should also be recognized that the process of the invention conveniently makes use of the exotherm produced by the acid-base reaction of the acetic solution with sodium aluminate to help raise the vessel temperature to the desired reaction temperature, thereby minimizing the energy input expenditure to provide a more favorable economic profile of the overall process.

The resulting product comprising aluminum diacetate monobasic that is formed in step (b) may be filtered and washed with water to remove residual NaCl, and any excess acetic acid and/or residual sodium acetate that may be present. The aluminum diacetate monobasic product is water insoluble, which allows efficient removal of sodium chloride and any excess acetic acid or residual sodium acetate by aqueous washing of the product filter cake with minimal loss of desired product. The wet filter cake can be used for various applications as is, or it can be dried to a suitable level depending on the requirement of the particular application. The product obtained by the process of this invention gives a composition having 15.4% to 18.3% aluminum by weight and 57% to 78% acetate by weight. At the lower temperature range of the process of this invention, starting at 50° C., even higher aluminum-percentage and lower acetate-percentage values are observed due to incomplete reaction. Preferably, the composition of the resulting aluminum diacetate monobasic salt is 16–17% aluminum by weight and 69–76% acetate by weight. Theoretically, pure, dry aluminum diacetate monobasic is 16.64% aluminum by weight and 72.86% acetate by weight. Vide infra from the empirical formula, these theoretical values provide an acetate-to-aluminum mole ratio of 2.0.

The present invention may be better understood by reference to the following non-limiting Example. The following Example is presented in order to more fully illustrate the preferred embodiments of the invention, and should in no way be construed as limiting the scope of the present invention.

EXAMPLE

Aluminum diacetate monobasic (ADAM) was prepared in accordance with the various experimental conditions summarized in Table 1. The use of 100% acetic anhydride during the initial mixing of the acetic anhydride and the sodium aluminate solution reached 105–106° C. very rapidly with no external heat applied. This implies that hot spots in the reaction vessel were likely present causing a formation of cross-linked Al—O species. This cross-linking phenomenon would necessarily result in a higher aluminum-percentage and a lower acetate-percentage due to the hydrolysis and elimination of acetate from the aluminum center. The formation of cross-linked Al—O species due to the strong exotherm from the rapid mixing of acetic anhydride and sodium aluminate solution is further supported by the high (2.2% v/v) residue level of the product in strong acid solution. However, acetic acid solutions produced from the aqueous hydrolysis of acetic anhydride and subsequently used in the process of this invention to produce aluminum diacetate monobasic gave satisfactory results. A controlled, slow addition of acetic anhydride to sodium aluminate solution gave good results, as did the use of mixed acetic acid/acetic anhydride solutions. The key factor when using acetic anhydride in the process of this invention is to avoid overheating or too rapid heating of the reaction mass.

TABLE 1

Summary of Reactions

| Rxn # | $NaAlO_2$ (moles) | NaOH (moles) | HOAc (moles) | $AlCl_3$ (moles) | ADAM Theor'l (moles) | ADAM Actual (moles) | Rxn Temp (° C.) | Step 1 Rxn (hrs) | Step 2 Rxn (hrs) | Yield (%) |
|---|---|---|---|---|---|---|---|---|---|---|
| 1 | 1.234 | 0.370 | 4.222 | 0.535 | 1.769 | 1.535 | 100 | 1 | 1 | 86.8 |
| 2 | 1.234 | 0.424 | 4.371 | 0.551 | 1.781 | 1.092 | 50 | 1 | 1 | 61.3 |
| 3 | 1.234 | 0.370 | 4.222 | 0.535 | 1.769 | 1.555 | 100 | 1 | 1 | 87.9 |
| 4 | 1.234 | 0.424 | 2.185* | 0.551 | 1.781 | 1.540 | 100 | 1 | 1 | 86.7 |
| 5 | 1.234 | 0.424 | 4.371 | 0.551 | 1.781 | 1.599 | 100 | 4 | 4 | 89.8 |
| 6 | 1.234 | 0.424 | 4.371 | 0.523 | 1.757 | 1.560 | 100 | 1 | 1 | 88.8 |
| 7 | 9742 | 3256 | 25540 | 3221 | 21823 | 19846 | 100 | 1 | 1 | 90.9 |
| 8 | 177.2 | 53.80 | 652.0 | 149.4 | 326.6 | 318.4 | 100 | 1 | 1 | 97.5 |
| 9 | 0.733 | 0.303 | 2.597 | 0.344 | 1.072 | 0.988 | 100 | 1 | 1 | 92.2 |
| 10 | 1.234 | 0.424 | 4.371 | 0.551 | 1.785 | 1.662 | 100 | 1 | 1 | 93.3 |
| 11 | 1.234 | 0.369 | 4.743 | 0.533 | 1.767 | 1.680 | 100 | 1 | 1 | 95.1 |
| 12 | 1.234 | 0.369 | 4.743 | 0.533 | 1.767 | 1.613 | 100 | 1 | 1 | 91.3 |
| 13 | 1.234 | 0.449 | 4.634 | 0.561 | 1.795 | 1.589 | 100 | 1 | 1 | 88.5 |
| 14 | 1.234 | 0.308 | 4.210 | 0.514 | 1.748 | 1.631 | 100 | 1 | 1 | 93.3 |
| 15 | 1.234 | 0.308 | 4.410 | 0.514 | 1.748 | 1.686 | 80 | 1 | 1 | 96.4 |
| 16 | 1.234 | 0.308 | 4.210 | 0.514 | 1.748 | 1.559 | 100 | 1 | 1 | 89.2 |
| 17 | 1.234 | 0.308 | 4.410 | 0.514 | 1.748 | 1.672 | 100 | 1 | 1 | 95.6 |
| 18 | 1.234 | 0.308 | 4.410 | 0.514 | 1.748 | 1.617 | 90 | 1 | 1 | 92.5 |
| 19 | 1.234 | 0.308 | 4.410 | 0.514 | 1.748 | 1.638 | 100 | 1 | 1 | 93.7 |
| 20 | 1.234 | 0.308 | 4.410 | 0.514 | 1.748 | 1.575 | 100 | 1 | 1 | 90.1 |
| 21 | 1.234 | 0.308 | 4.410 | 0.514 | 1.748 | 1.528 | 100 | 1 | 1 | 87.4 |
| 22 | 1.234 | 0.308 | 4.410 | 0.514 | 1.748 | 1.159 | 100 | 1 | 1 | 66.3 |
| 23 | 0.617 | 0.154 | 1.923 | 0.000 | 0.617 | 0.574 | 100 | 1 | 1 | 93.0 |
| 24 | 1.234 | 0.308 | 4.410 | 0.514 | 1.748 | 1.100 | 100 | 0.5 | 0.5 | 62.9 |
| 25 | 1.234 | 0.308 | 3.492 | 0.508 | 1.742 | 1.299 | 100 | 2 | 1 | 74.6 |
| 26 | 1.234 | 0.308 | 3.493 | 0.508 | 1.742 | 1.255 | 100 | 0.5 | 2 | 72.0 |
| 27 | 1.536 | 0.547 | 4.960 | 0.616 | 2.152 | 1.644 | 100 | 0.5 | 0.5 | 76.4 |
| 28 | n/a | n/a | 1.234 NaOAc | 0.411 | 0.411 | 0.390 | 100 | n/a | 1 | 94.9 |

*moles of acetic anhydride instead of acetic acid as investigated in Reaction #4, gave a poor acetate-to-aluminum ratio (high aluminum-%, low acetate-%) in the desired product. The exotherm produced The aluminum content of $Al(C_2H_3O_2)_2OH$ material produced by the process of this invention was determined by a complexometric method using CDTA as the aluminum chelating agent. This analytical method for aluminum was calibrated with an Al standard before and after duplicate sample analysis. The acetate content of the material produced by the process of this invention was determined by liquid chromatographic means employing a C18 polymer (Astec) column with 0.5 M $KH_2PO_4$ mobile phase buffered to pH 2.5 delivered at a 1.5 ml/min flow rate, and UV detection at 200 nm. A system suitability check of the LC system and method was performed before replicate sample analysis of aluminum diacetate monobasic material produced by this invention. Additionally, the validity of the data for Al and acetate content obtained by the methods described above was confirmed through elemental analysis (Al, C, O, H) by an independent laboratory.

In order to measure the amount of insoluble residue of the aluminum diacetate monobasic in acid solutions, the following test procedure was employed. In this test, one gram of the dried material was placed in a 250 ml flask and 90 ml of 40% (v/v) HCl solution was added. This mixture was magnetically stirred for 5 minutes and poured into a graduated, conical bottom 100 ml sedimentation tube. An additional 10 ml of the 40% HCl solution was used to rinse the flask and the rinse added to the sedimentation tube. After 30 minutes, the level of solid material was recorded and a % residue by volume value obtained. This data is provided in Table 2.

TABLE 2

Reaction Results

| Rxn # | MgCO$_3$ Treated | Na (%) | Cl (%) | Residue (vol-%) | Al (wt-%) | >Oac (wt-%) | >OAc/Al ratio |
|---|---|---|---|---|---|---|---|
| 1 | yes | 0.240 | 0.414 | 0.020 | 17.89 | 70.47 | 1.800 |
| 2 | no | 0.417 | 0.799 | 0.500 | 20.40 | 57.02 | 1.277 |
| 3 | no | 0.079 | 0.410 | 0.150 | 17.89 | 71.36 | 1.823 |
| 4 | no | 0.057 | 0.300 | 2.200 | 18.28 | 67.26 | 1.681 |
| 5 | no | 0.053 | 0.220 | 0.130 | 17.345 | 77.80 | 2.050 |
| 6 | no | 0.042 | 0.196 | 0.090 | 17.74 | 75.80 | 1.952 |
| 7 | yes | 1.090 | 1.620 | <0.02 | 16.37 | 72.19 | 2.015 |
| 7a | yes | 0.884 | 1.320 | 0.020 | 16.45 | 71.12 | 1.975 |
| 7b | yes | 2.230 | 3.390 | 0.030 | 15.68 | 69.14 | 2.015 |
| 7c | yes | 1.840 | 2.850 | <0.02 | 15.73 | 68.30 | 1.977 |
| 7d | yes | 1.300 | 1.980 | <0.02 | 16.00 | 67.07 | 1.913 |
| 7e | yes | 1.460 | 2.160 | 0.030 | 16.21 | 68.97 | 1.944 |
| 7f | yes | 2.210 | 3.350 | <0.03 | 15.41 | 69.49 | 2.060 |
| 8 | yes | 0.150 | 0.500 | 0.050 | 17.11 | 74.70 | 1.995 |
| 9 | yes | 0.039 | not tested | 0.040 | 17.03 | 70.25 | 1.885 |
| 10 | no | 0.030 | not tested | 0.060 | 16.97 | 70.48 | 1.898 |
| 11 | no | 0.022 | 0.448 | 0.050 | 16.66 | 72.87 | 1.998 |
| 12 | no | 0.050 | 0.369 | 0.550 | 17.58 | 68.83 | 1.784 |
| 13 | no | 0.030 | 0.346 | 0.500 | 17.99 | 71.73 | 1.822 |
| 14 | no | 0.010 | 0.260 | 0.300 | 17.12 | 72.72 | 1.940 |
| 15 | no | 0.040 | 0.320 | 0.150 | 16.70 | 70.80 | 1.937 |
| 16 | no | 0.020 | 0.430 | 0.300 | 17.01 | 70.96 | 1.906 |
| 17 | no | 0.030 | 0.300 | 0.200 | 16.02 | 72.2 | 2.059 |
| 18 | no | 0.030 | 0.380 | 0.350 | 16.25 | 72.34 | 2.034 |
| 19 | no | 0.040 | 0.440 | 0.400 | 16.78 | 74.33 | 2.024 |
| 20 | no | 0.040 | 0.260 | 0.600 | 16.99 | 72.35 | 1.946 |
| 21 | no | 0.014 | 0.364 | not tested | 16.56 | 73.26 | 2.021 |
| 22 | no | 0.060 | 0.210 | not tested | 18.14 | 69.13 | 1.741 |
| 23 | no | 0.632 | 0.860 | not tested | 14.66* | 64.30* | 2.006 |
| 24 | no | 0.007 | 0.250 | not tested | 17.61 | 68.40 | 1.775 |
| 25 | no | 0.240 | 0.390 | not tested | 18.31 | 68.32 | 1.705 |
| 26 | no | 0.430 | 0.730 | not tested | 18.38 | 64.90 | 1.613 |
| 27 | no | 0.084 | 1.680 | not tested | 17.33 | 67.47 | 1.779 |
| 28 | no | 0.028 | 0.430 | 0.000 | 16.23 | 73.63 | 2.073 |

*not sufficiently dried, LOD = 6.51-wt%

Vibrational spectroscopy was used to analyze the $Al(C_2H_3O_2)_2(OH)$ material produced by this invention whereby the infrared spectrum of the material in a KBr matrix was obtained using a Fourier transform infrared (FT-IR) spectroscopic instrument. The relevant absorbances and their assignments based on infrared spectrum of the $Al(C_2H_3O_2)_2(OH)$ material produced by the present invention are given in the Table 3 below.

TABLE 3

Infrared Spectroscopy Results

| Frequency (cm$^{-1}$) | Description | Assignment | Reference |
|---|---|---|---|
| 3700 | intense, narrow | non-H bonded, free hydoxyl | 23, 24 |
| 3472 | strong, broad | —OH, —COOH stretching | 27, 8 |
| 1600 | strong | —C═O stretching, antisymmetrical | 26, 24 |
| 1476, 1427 | strong | —C═O stretching, symmetrical (two bands due to two —COOHs) | 24, 25, 26 |
| 1360 | narrow, medium | symmetrical —CH$_3$ deformation | 26, 27 |
| 1264 | weak | coupled C—O and OH in-plane deformation | 26 |
| 1062 | sharp, moderate | —OH bending (typical of boehmite-like structures) | 8, 28 |
| 985 | strong | Al—O linkage | 24, 25, 28 |
| 682, 652, 695, 625 | strong, split into various bands | Al—O stretching | 26, 28 |
| 500, 570 | strong, split into various bands | Al—O stretching | 26, 8, 28 |

The sharp, intense band at 3700 cm$^{-1}$ is indicative of a hydroxide moiety that has little or no hydrogen bonding. In samples of wet cake and insufficiently dried aluminum diacetate monobasic, there exists enough water content to provide some degree of hydrogen bonding that has the effect on the IR spectrum of diminishing the intensity and broadening the band assigned to the free hydroxide. This moisture effect can be pronounced enough such that the band at 3700 cm$^{-1}$ is not observed at all. The broad strong absorbance at 3472 cm$^{-1}$ is typical of carboxylic acids and their salts. The strongest bands in the spectrum at 1600, split bands at 1475, 1427, and at 900 cm$^{-1}$ are characteristic of aluminum diacetate monobasic.

Aluminum diacetate monobasic material produced in the laboratory and at plant-scale was analyzed for phase purity and identification by X-ray powder diffraction analysis using Cu K$_\alpha$ incident radiation at a wavelength of 1.540562 Å. The samples from the lab and plant process gave powder patterns that matched the reference pattern for aluminum diacetate monobasic kept on file with the Joint Commission on Powder Diffraction Studies/International Centre for Diffraction Data. The powder pattern of the material produced by the process of this invention was indexed and this data used to determine the refined unit cell parameters. The unit cell data for aluminum diacetate monobasic prepared by the process of this invention describes a material crystallizing in an orthorhombic system in space group Ccc2 (n. 37) having cell edges of a=14.10152 Å, b=6.98336 Å and c=6.6829 Å. The refined unit cell volume was 658.11 Å$^3$. This data correlates with that reported in the literature and prior art.

sodium chloride due to insufficient aqueous washing of the product filter cake.

Figure 1:
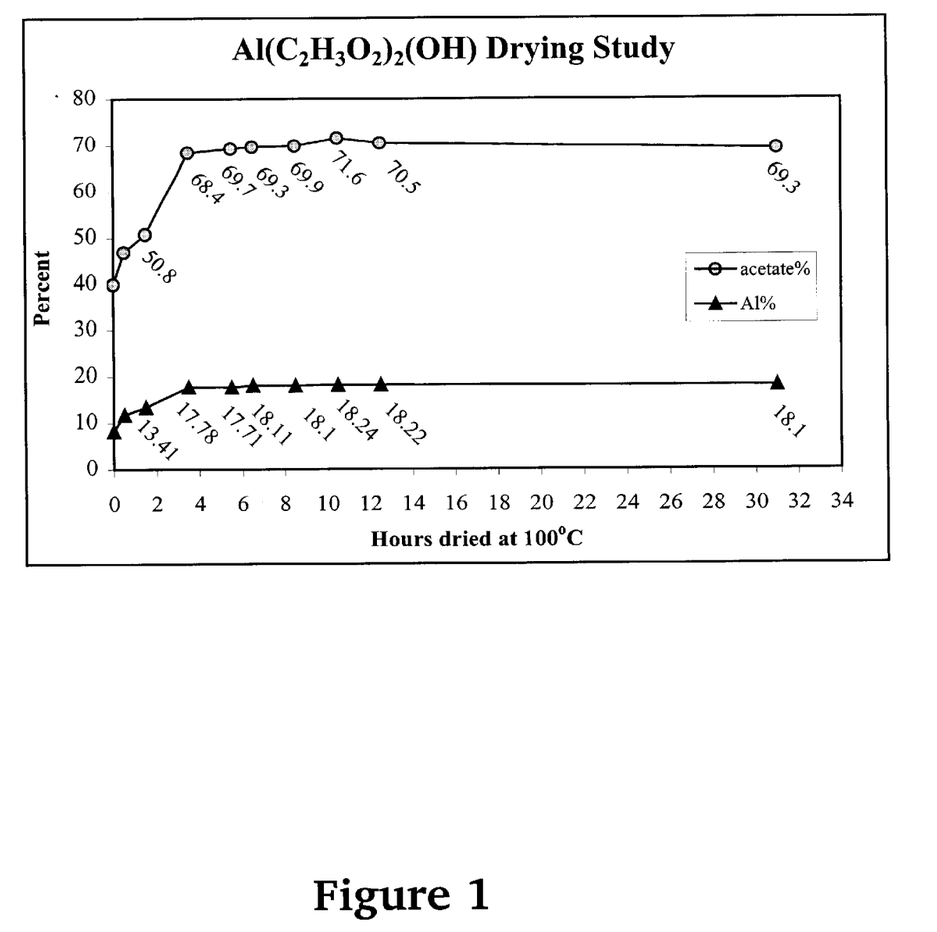
FIG. 1 is graph showing the relation between drying time in hours at 100° C. of $Al(C_2H_3O_2)_2(OH)$ versus the % aluminum and % acetate content in the composition.
Figure 2:
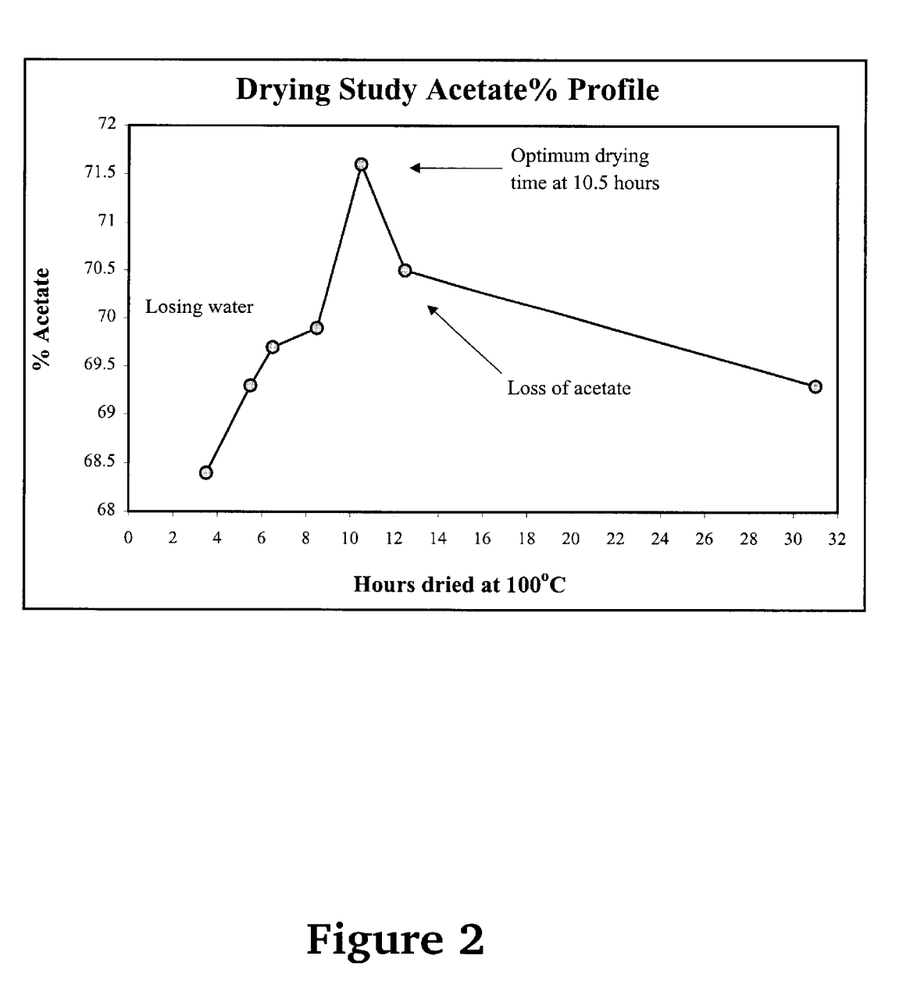
FIG. 2 is a reduced scale graph showing the behavior of % acetate content in relation to time during the drying process of $Al(C_2H_3O_2)_2(OH)$ at 100° C.

A drying study of the wet cake material from the process was performed. The wet cake was placed in a 100° C. oven with samples removed and analyzed at various time intervals. Merkl states in U.S. Pat. No. 3,957,598, issued May 18, 1976, that aluminum diacetate loses acetic acid upon heating and insoluble material begins to form as aluminum-to-oxygen bonding occurs. The structure and nature of that resulting insoluble oxo-aluminum is disputed, but it can be reasonably assumed that a process of aluminum to oxygen cross-linking occurs forming some type of polymeric or extended structure aluminum compound or compounds. When the reaction temperature of step (a) or step (b) of the current invention exceeds 105° C., or when the drying temperature of the wet cake material exceeds 105° C., the formation of aluminum-containing acid insoluble material, discussed by Merkl, is observed. FIG. 1 depicts the plot of aluminum content and acetate content as a function of time during the course of the drying study. The relevant portion of the drying study pertaining to the behavior of the %-acetate content is depicted in FIG. 2, and this profile indicates a maximum acetate content at 10.5 hours of drying at 100° C. which is followed immediately by a drop off in the plot (loss of acetate), as drying is continued.

Figure 3:
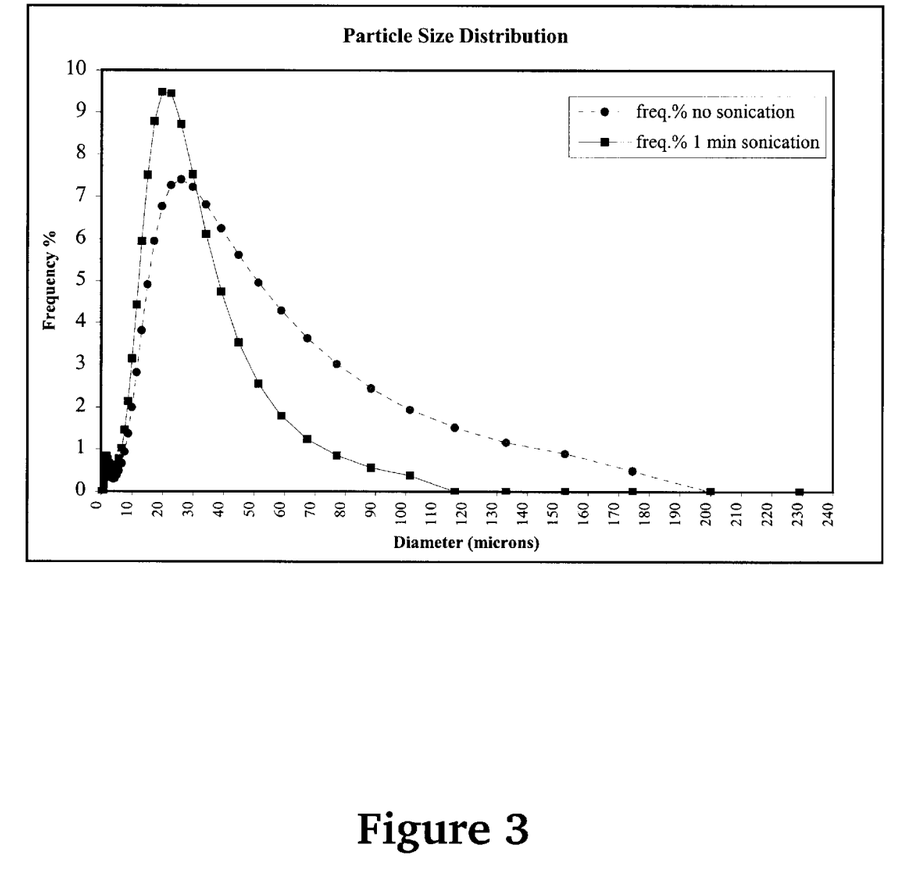
FIG. 3 is an overlay graph depicting the particle size distribution analysis [frequency % versus particle diameter ($\mu$/m)] of an $Al(C_2H_3O_2)_2(OH)$ sample obtained with a laser scattering instrument. The compared plots represent analysis with no sonication, and after one minute of sonication.

The particle size distribution of the insoluble Al(C$_2$H$_3$O$_2$)$_2$(OH) material produced by the process of the present invention ranges from 0.5 μm to 125 μm, but typically and preferably is in the range of 20 μm to 50 μm for the majority (≧75%) of the individual particles. FIG. 3 provides an overlay of the samples particle size distribution curves without sonication, and with one minute of sonication.

TABLE 4

X-ray Powder Diffraction Pattern Data for Aluminum Diacetate Monobasic

| Peak # | 2θ (°) Calc'd | 2θ (°) Obs'd | Difference (Calc'd-Obs'd) | h | k | l | Calculated d-Line (Å) | Observed d-Line (Å) | Difference (Calc'd-Obs'd) | I% |
|---|---|---|---|---|---|---|---|---|---|---|
| 1 | 12.544 | 12.541 | 0.0030 | 2 | 0 | 0 | 7.0508 | 7.0526 | −0.0019 | 32.0 |
| 2 | 14.141 | 14.119 | 0.0210 | 1 | 1 | 0 | 6.2580 | 6.2674 | −0.0094 | 100 |
| 3 | 19.416 | 19.380 | 0.0360 | 1 | 1 | 1 | 4.5679 | 4.5763 | −0.0083 | 33.0 |
| 4 | 22.786 | 22.798 | −0.0120 | 3 | 1 | 0 | 3.8994 | 3.8974 | 0.0021 | 24.0 |
| 5 | 25.489 | 25.497 | −0.0080 | 0 | 2 | 0 | 3.4917 | 3.4906 | 0.0011 | 3 |
| 6 | 26.442 | 26.440 | 0.0020 | 3 | 1 | 1 | 3.3680 | 3.3683 | −0.0003 | 27.0 |
| 7 | 29.559 | 29.540 | 0.0190 | 2 | 0 | 2 | 3.0195 | 3.0214 | −0.0019 | 8 |
| 8 | 30.297 | 30.242 | 0.0550 | 1 | 1 | 2 | 2.9476 | 2.9529 | −0.0053 | 8 |
| 9 | 31.545 | 31.501 | 0.0440 | 2 | 2 | 1 | 2.8338 | 2.8377 | −0.0039 | 1 |
| 10 | 36.178 | 36.199 | −0.0210 | 4 | 2 | 0 | 2.4808 | 2.4794 | 0.0014 | 10.0 |
| 11 | 36.879 | 36.900 | −0.0210 | 5 | 1 | 1 | 2.4353 | 2.4339 | 0.0014 | 6 |
| 12 | 38.683 | 38.699 | −0.0160 | 4 | 2 | 1 | 2.3257 | 2.3248 | 0.0009 | 7 |
| 13 | 39.192 | 39.200 | −0.0080 | 1 | 3 | 0 | 2.2967 | 2.2963 | 0.0004 | 2 |
| 14 | 41.543 | 41.559 | −0.0160 | 1 | 3 | 1 | 2.1720 | 2.1712 | 0.0008 | 1 |
| 15 | 43.066 | 43.020 | 0.0460 | 1 | 1 | 3 | 2.0986 | 2.1008 | −0.0022 | 4 |
| 16 | 45.500 | 45.461 | 0.0390 | 4 | 2 | 2 | 1.9919 | 1.9935 | −0.0016 | 1 |
| 17 | 46.541 | 46.600 | −0.0590 | 6 | 2 | 0 | 1.9497 | 1.9474 | 0.0023 | 4 |
| 18 | 46.935 | 46.939 | −0.0040 | 3 | 1 | 3 | 1.9343 | 1.9341 | 0.0002 | 2 |
| 19 | 48.604 | 48.439 | 0.1650 | 6 | 2 | 1 | 1.8717 | 1.8777 | −0.0060 | 4 |
| 20 | 50.816 | 50.840 | −0.0240 | 5 | 3 | 0 | 1.7953 | 1.7945 | 0.0008 | 3 |
| 21 | 51.610 | 51.581 | 0.0290 | 3 | 3 | 2 | 1.7695 | 1.7704 | −0.0090 | 2 |
| 22 | 51.824 | 51.860 | −0.0360 | 8 | 0 | 0 | 1.7627 | 1.7616 | 0.0011 | 1 |
| 23 | 54.070 | 54.099 | −0.0300 | 2 | 4 | 0 | 1.6947 | 1.6938 | 0.0009 | 2 |
| 24 | 54.440 | 54.440 | 0.0000 | 6 | 2 | 2 | 1.6840 | 1.6840 | 0.0000 | 2 |
| 25 | 54.909 | 54.978 | −0.0690 | 0 | 0 | 4 | 1.6707 | 1.6688 | 0.0019 | 1 |

The lab-produced material was essentially free from NaCl impurity by X-ray powder diffraction, but samples of plant-scale material did show some trace contamination with The overall effect of sonication in this type of analysis is to de-agglomerate particles to give an absolute particle size distribution. Significant shifts in the distribution curve maxima to smaller particle size would indicate that the particles were agglomerated, but it could also be indicative of particles that have a low degree of individual stability and are broken up due to the effect of the sonication. The particle distribution analysis for the $Al(C_2H_3O_2)_2(OH)$ material prepared by the process of this invention shows that the material is not significantly agglomerated and that the individual particles are quite stable.

Bulk density measurements of the spray-dried aluminum diacetate monobasic produced at plant-scale were made. A plant campaign was conducted (Reaction #7 in Table 1), producing aluminum diacetate monobasic in six batch lots (Reaction #'s 7a–f). Samples of each batch lot were tested for bulk density. The individual results were 0.585 g/ml, 0.582 g/ml, 0.588 g/ml, 0.591 g/ml, 0.580 g/ml and 0.581 g/ml, yielding an average bulk density value of 0.585 g/ml (±0.004 g/ml).

CITED REFERENCES

1. V. N. Maksimov, et al., Zhur. Neorg. Khim., 5: 558 (1960) [*Russ. J. Inorg. Chem.,* 267, 1960].
2. *Aluminium, Its Applications in the Chemical and Food Industry,* P. Junière and M. Sigwalt (translated from French by W. C. E. Barnes), Chemical Publishing Company: New York, N.Y., p. 78, 1964.
3. W. Crum, *Annalen,* 59:156 (1854).
4. Ley, *Z. phys. Chem.,* 30: 245 (1899).
5. Hennig, *Chem. Zentr.,* 4161 (1936).
6. British Patent No. 452065.
7. PCT Appn. Publication No. WO 97/41063, published November, 1996.
8. PCT Appn. Publication No. WO 98/47849, published October, 1998.
9. Sears, U.S. Pat. No. 2,992,262, issued July, 1961.
10. Weinland, *Ber.,* 47: 2756 (1914).
11. Hood, *J. Amer. Chem. Soc.,* 72: 2094 (1950).
12. Reinhardt, et al., U.S. Pat. No. 4,224,030, issued September, 1980.
13. Funk, *Z. anorg. Chem.,* 199: 94 (1931).
14. Spath, *Monatsch.,* 33: 235 (1912).
15. Seligman, *J. Soc. Chem. Ind,* 35: 88 (1916).
16. Merkil, U.S. Pat. No. 3,957,598, issued May, 1969.
17. Bumans and Mironovich, *Latv. PSR Zinat. Akad. Vestis, Kim. Ser.,* 2: 167–170 (1974); CA 81: 32638.
18. Johnson, U.S. Pat. No. 3,014,055, issued December, 1961.
19. Shih, U.S. Pat. No. 3,655,329, issued April, 1972.
20. Sharif, U.S. Pat. No. 5,233,065, issued August, 1993.
21. V. N. Maksimov and A. I. Grigor'ev, *Russ. J. Inorg Chem.* (Engl.), 9(4): 559–560 (1964).
22. JCPDS/ICDD, International Centre for Diffraction Data, 1601 Park Lane, Swarthmore, Pa. 19081–2389, 2000.
23. K. Nakamoto; M. Margoshes; and R. E. Rundle, "Stretching Frequencies as a Function of Distances in Hydrogen Bonds," *J. Am. Chem. Soc.,* 77: 6480 (1955).
24. F. A. Scott; J. Goldenson; S. E. Wiberley; and W. H. Bauer, "Infrared Spectra of Aluminum Soaps and Soap-Hydrocarbon Gels," *J. Phys. Chem.,* 58: 61 (1954); 77: 6480 (1955).
25. A. I. Grigor'ev, "Infrared Absorption Spectra of Acetates of Elements in Groups I and II of the Periodic System," *Russ. J. Inorg. Chem. (Engl.),* 409 (1963).
26. L. J. Bellamy, *The Infrared Spectra of Complex Molecules,* John Wiley & Sons: New York, 1962.
27. J. A. Dean, *Analytical Chemistry Handbook,* McGraw Hill: New York, 1995.
28. V. C. Farmer, Ed., *The Infrared Spectra of Minerals,* The Mineralogical Society, 1974.

All publications mentioned herein above, whether to issued patents, published applications, published articles, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A process for preparing aluminum diacetate monobasic comprising the steps of: (a) agitating a reaction mixture comprising an aqueous acetic solution and a sodium aluminate solution to form aluminum diacetate monobasic and sodium acetate in the reaction mixture; and (b) adding aluminum chloride solution to the reaction mixture in an amount sufficient to react with sodium acetate to obtain a resulting product comprising aluminum diacetate monobasic.

2. The process of claim 1, wherein the aqueous acetic solution comprises acetic acid.

3. The process of claim 1, wherein the aqueous acetic solution comprises acetic anhydride.

4. The process of claim 1, wherein the aqueous acetic solution comprises a combination of acetic acid and acetic anhydride.

5. The process of claim 1, wherein the sodium aluminate solution contains 1–45% by wt. sodium aluminate.

6. The process of claim 1, wherein the sodium aluminate solution contains 38–45% by wt. sodium aluminate.

7. The process of claim 1, wherein the sodium aluminate solution is subjected to treatment with magnesium carbonate followed by filtration before being admixed with the aqueous acetate solution in step (a).

8. The process of claim 7, wherein the treatment of sodium aluminate solution with magnesium carbonate comprises the steps of: (i) heating the sodium aluminate solution to a minimum temperature of 80° C.; (ii) adding magnesium carbonate to the heated sodium aluminate solution in a concentration ranging from 0.005% to 10.0% by weight; (iii) agitating the magnesium carbonate treated sodium aluminate solution for 30 minutes to 24 hours; and (iv) filtering the agitated, magnesium carbonate treated sodium aluminate solution to remove acid-insoluble material, base-insoluble material and magnesium-chelated organic anions.

9. The process of claim 8, wherein the concentration of magnesium carbonate added in step (ii) ranges from 0.01% to 0.1% by weight.

10. The process of claim 8, wherein the concentration of magnesium carbonate added in step (ii) is about 0.05% by weight.

11. The process of claim 8, wherein the magnesium carbonate treated sodium aluminate solution is agitated in step (iii) for 30 minutes to 4 hours.

12. The process of claim 8, wherein after step (iii) and before step (iv), the agitated, magnesium carbonate treated sodium aluminate solution is cooled to a temperature of 80° C. to 25° C.

13. The process of claim 8, wherein the agitated, magnesium carbonate treated sodium aluminate solution is cooled to a temperature of 80° C. to 25° C. over a period of 12–24 hours.

14. The process of claim 1, wherein the aluminum chloride solution contains 10–31% by wt. aluminum chloride.

15. The process of claim 1, wherein the aluminum chloride solution contains 25–31% by wt. aluminum chloride.

16. The process of claim 1, wherein step (a) is conducted at a temperature of 50–105° C.

17. The process of claim 1, wherein step (a) is conducted at a temperature of 95–100° C.

18. The process of claim 1, wherein step (a) is conducted for 1–8 hours.

19. The process of claim 1, wherein step (b) is conducted at a temperature of 50–105° C.

20. The process of claim 1, wherein step (b) is conducted at a temperature of 95–100° C.

21. The process of claim 1, wherein step (b) is conducted for 1–8 hours.

22. The process of claim 1, wherein the resulting product formed in step (b) is filtered and washed with water to remove residual NaCl, and any excess acetic acid and residual sodium acetate.

* * * * *